Figure 1:
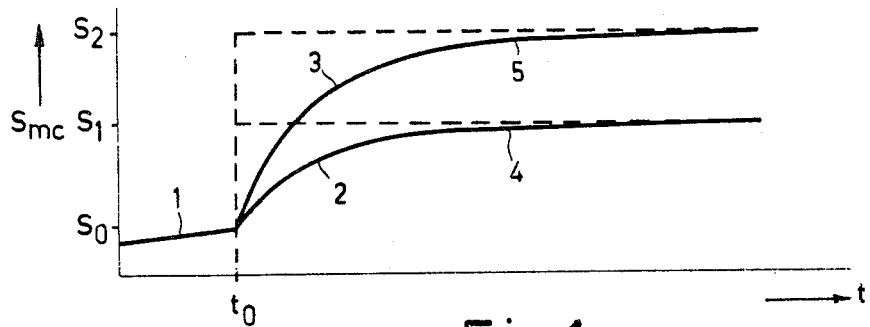

United States Patent [19]
Kruishoop

[11] 3,949,599
[45] Apr. 13, 1976

[54] METHOD OF QUANTITAVE ANALYSIS
[75] Inventor: Johan Christiaan Willem Kruishoop, Eindhoven, Netherlands
[73] Assignee: U.S. Philips Corporation, New York, N.Y.
[22] Filed: Oct. 17, 1974
[21] Appl. No.: 515,701

[30] Foreign Application Priority Data
Oct. 27, 1973 Netherlands............... 7314801

[52] U.S. Cl..................... 73/61.1 R; 73/1 R; 73/28
[51] Int. Cl.².......................................... G01N 27/50
[58] Field of Search............... 73/61.1 R, 1 R, 23, 28

[56] References Cited
UNITED STATES PATENTS
3,247,702  4/1966  Houser et al..................... 73/1 R
3,611,790  10/1971 Brouwer et al. ................. 73/61.1 R Primary Examiner—Richard C. Queisser
Assistant Examiner—Joseph W. Roskos
Attorney, Agent, or Firm—Frank R. Trifari; Bernard Franzblau

[57] ABSTRACT

For continuously and quantitatively determining one or more constituents of a fluid a given amount thereof is passed through a measuring cell which has an adjustment inertia of exponential nature. By alternately passing a reference fluid and the fluid to be measured through the measuring cell at a rate at which only part of the adjustment characteristic is used a sawtooth measuring signal is obtained at the measuring cell which by electronic processing and filtering rapidly provides information about the amount to be determined of the said constituents. The resulting signal may be used to control a variable calibrating system or it may, because continuous calibrating is also found to be possible, be used for instantaneous accurate indication of the measuring value.

16 Claims, 7 Drawing Figures

METHOD OF QUANTITAVE ANALYSIS

The invention relates to a method of continuously and quantitatively determining one or more constituents of a fluid in which a given quantity of the fluid is passed through a measuring cell having measuring elements at which a measuring signal is produced which is a measure of the quantity of the constituents to be measured, said cell having a response inertia of exponential nature.

U.S. Pat. No. 3,611,790 describes methods and apparatus by means of which constituents of a fluid can accurately be measured. A measuring cell is used which is sensitive to the presence of given substances or particles. To obtain a continuous analysis of the fluid, a flow of the fluid to be measured is passed through the measuring cell. This cell may be designed so as to deliver an electric signal which is representative of the amount of constituents to be measured and is supplied per unit time. The patent describes that in the conversion and measuring processes in the measuring cell there are various parameters which determine the measuring accuracy and which ultimately influence the electric output signal of the cell. By measuring the zero drift and calibrating the cell at regular intervals the said influences can largely be eliminated.

In this known measuring system it is required that during the respective periods of zero-point determination, calibration and measurement the various parameters should be constant, cf., the said patent, column 2, lines 58 to 65. If the parameters vary rapidly in time, the measuring period may obviously be interrupted for shorter intervals for zero point determination and calibration.

For some measurements the said zero point and calibration interruptions may be undesirable because calibration of the cell requires an unduly long period of time at the expense of the measuring time.

The cause of the said long periods of time generally is that the measuring cell is slow in adjusting to a new valve. To a sudden change in concentration of the constituents to be measured, many measuring cells have a response curve the initial part of which is exponential and which finally creeps to the new measuring value.

The invention is based on the recognition that the said exponential response curve of a measuring cell can be used to perform the desired measurements, for it has been found that for short-term operation the said characteristic is reproducible and constant and that any long-term variation can simply be determined by calibration and then corrected.

The method according to the invention is characterized in that during a time T in which only part of the exponential response characteristic of the measuring cell is used, a reference fluid containing a known amount of constituents to be measured and the fluid to be measured are alternately passed through the measuring cell and the amount of constituents to be measured is determined by means of the resulting sawtooth measuring signal.

The advantages of this method are:

in a short time which is smaller by an integral factor than the analogous response time, information about the amount of constituents to be measured is obtained;

a zero signal which is delivered by the cell in the absence of the constituents to be measured and which may vary with time can simply be eliminated;

the linearity can be improved by displacing the measuring region to a linear part of the measuring curve by means of a calibrating or reference fluid;

the noise in the measuring signal can more simply be eliminated by choosing the time T in connection with electronic filters.

By measuring and filtering the sawtooth component from the measuring signal of the measuring cell a quantity is obtainable which is a measure of the desired measuring value. The quantity may be further processed or recorded but may alternatively be used as an input signal for a regulating circuit the output of which controls a variable calibrating source which determines the reference level in the reference fluid. Adjustment of the calibrating source then is the measure of the amount of constituents to be determined.

In a further elaboration of the method according to the invention, methods are proposed for processing the sawtooth measuring signal which advantageously reduce or eliminate the influence exerted by the various cell parameters on the measuring result.

Thus according to the invention preferably the reference fluid is prepared from the fluid to be measured by passing the latter through a cleaning filter in which the constituents to be measured are removed, and then supplying it to the measuring cell. Also, a known amount of the constituents to be measured may be added to the cleaned fluid at a point between the cleaning filter and the measuring cell.

This provides the advantage that the influence of the non-specificity, that is to say the sensitivity of the measuring cell to constituents other than those to be measured, is reduced and hence the selectivity is increased.

Another elaboration of the method according to the invention is characterized in that for pairs of successive periods of duration T the sum of the integrated value of the sawtooth measuring signal during the first half of the second period and A times the integrated value during the second part of the first period is determined, and also the sum of the integrated value of the measuring signal during the second half of the second period and A times the integrated value during the first half of the first period is determined, where A is a positive weighting factor smaller than, or equal to, unity, and in that the difference of the said sums is determined which is a measure of the amount to be determined of the constituents to be measured.

The latter method provides the advantage that the selectivity and the signal-to-noise ratio are increased. Furthermore it has been found that after two periods of duration T the amount of constituents to be determined is given by the said difference with a sufficient degree of accuracy.

The weighting factor can be unity if substantially linear portions of the response characteristic curve of the cell are used, which provides the advantage that interference voltages of linear form, such as the zero signal and non-specific signals, are completely eliminated. If it is found that the said interfering voltages do not have so large an influence relative to noise signals, the factor A must be given another value to find a compromise.

It has been found that the adjustment characteristic of many measuring cells can be expressed by a summation of powers of $e$, the main contribution to the characteristic being provided by an $e$ power of minimum time constant $T_1$ and maximum amplitude.

When the weighting factor A is made $\exp(-T/T_1)$ it is found that in the said cases abrupt changes in concentration also can be determined with a sufficient degree of accuracy after two periods. Obviously the duration T required to reach a favorable signal-to-noise ratio will cover a larger part of the exponential response characteristic.

A further elaboration of the said methods enables two fluid flows to be passed through a single measuring cell independently of one another.

A method according to the invention is characterized in that in order to measure two fluid flows, two measuring systems are arranged in parallel, one measuring cell is used, and the periods of time T are equal for both systems but the first system is shifted one half of a period in time relative to the second system. One fluid flow may be a calibrating flow so that continuously a calibrating signal is available to determine the sensitivity drift of the measuring cell and to correct the measured value thereby.

Owing to the use of the proposed method of integration, summation and differentiation, a calibrating signal can be derived from the measuring cell in another advantageous manner also, appropriate filtering providing an accurate separation between the measuring signals and the calibrating signal.

For this purpose a method according to the invention is characterized in that with a repetition time $T/2n$, where $n$ is an integer, a calibrating amount of constituents to be measured is introduced into the measuring cell, the sawtooth measuring signal is filtered electrically also at a frequency of $2n/T$ and the mean amplitude of the resulting filtered signal is measured and by means of a divider circuit a quantity is determined which, irrespective of the sensitivity variation of the measuring cell, is proportional to the amount to be determined of the constituents to be measured and which is equal to the said difference divided by the said mean amplitude.

Figure 2:
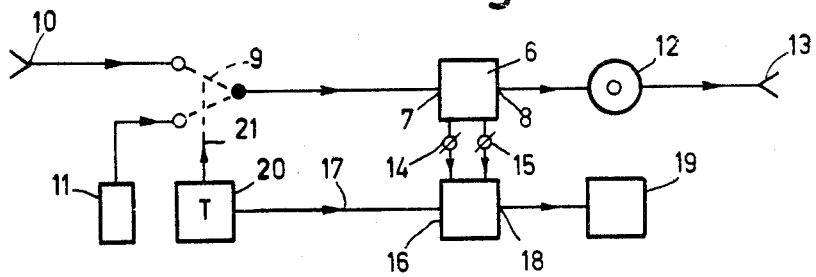
Figure 3:
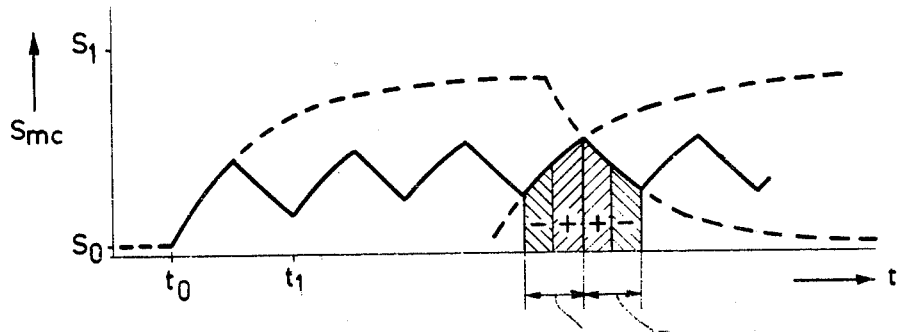
Figure 4:
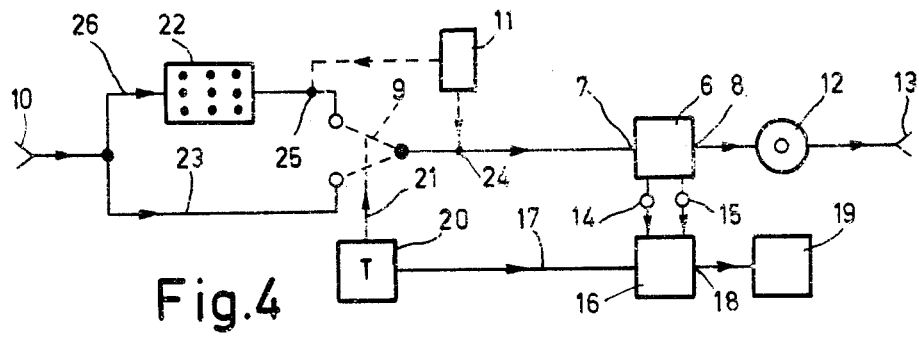
Figure 5:
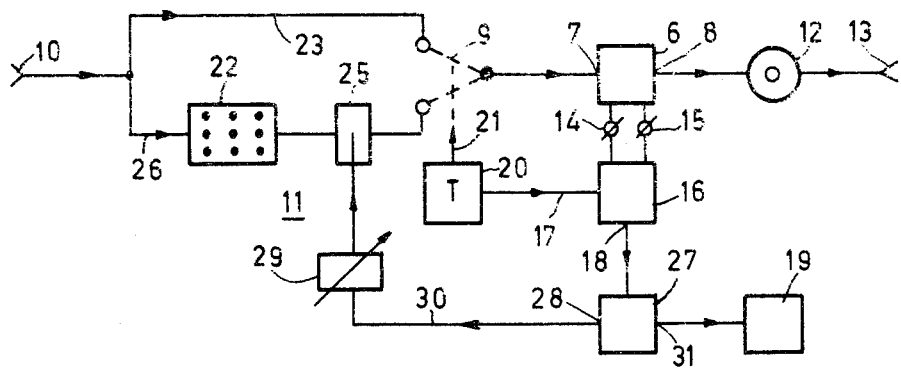
Figure 6:
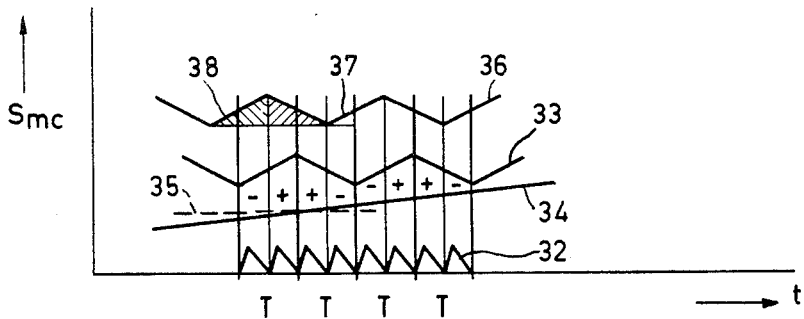
Figure 7:
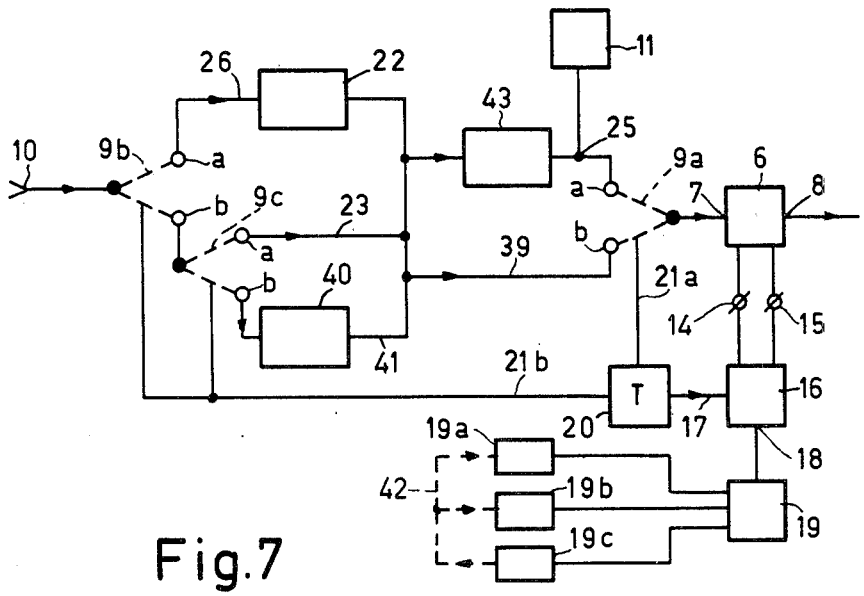

Embodiments of the invention will now be described, by way of example, with reference to the accompanying diagrammatic drawings, in which:

FIG. 1 is a diagram of an exponential response characteristic of a measuring cell, FIG. 2 is a block-schematic diagram of an apparatus by means of which the method according to the invention can be carried out, FIG. 3 is a diagram of the sawtooth measuring signal obtained at the measuring cell in the method according to the invention, FIG. 4 is a block-schematic diagram of an apparatus by means of which methods according to the invention can be carried out, FIG. 5 is a block schematic diagram of another apparatus, FIG. 6 is a diagram of the measuring signal of the measuring cell, which diagram shows two measuring signals, a calibrating signal and an interference signal, and FIG. 7 shows an apparatus for simultaneously measuring amounts of NO and of $NO_2$ by a method according to the invention.

Referring now to FIG. 1, a measuring signal $Smc$ derived from the terminals of a measuring cell capable of measuring constituents of a fluid is plotted along the vertical axis. Time $t$ is plotted along the horizontal axis.

Prior to an instant $t_0$ at which the constituents to be measured are admitted to the cell, the cell delivers a zero signal of value $S_0$ which varies in time, as is shown by a line 1. This signal may include the response of the cell to constituents other than those to be measured. At the instant $t_0$ the concentration of the constituents to be measured changes abruptly.

If the measuring cell were capable of responding at an infinitely fast rate, it would signal the sudden variation by giving a signal $S_1$ or a signal $S_2$ respectively. However, adjustment to these measured values is effected according to curves 2 and 3, respectively. Generally the first portion of the said curves, up to for example 90% of the final value, can be expressed as a power of $e$ having an exponent $-t/T_1$, for example $0.9S_1[1-\exp(-t/T_1)]$.

The tail portions 4 and 5 then can be expressed by $e$ powers of small amplitude and steadily increasing time constants.

FIG. 2 is a block-schematic diagram of an apparatus which includes a measuring cell 6 having an input 7 for supplying fluid and an output 8 for discharging it. A change-over valve 9 determines whether the flow is derived from the fluid to be measured, which is supplied via an inlet 10, or from a reference fluid, which is supplied by a source 11. The reference fluid contains a known amount of constituents to be measured, which amount may be zero.

The fluid flow is maintained by a pump 12 having a delivery outlet 13. The measuring signal $Smc$ shown in the diagram of FIG. 3 is taken from the cell 6 at measuring terminals 14 and 15. In a device 16 the measuring signal is measured under the control of a signal applied by a clock 20 via a lead 17. Thus at an output 18 of the device 16 a signal is produced which can be made visible and be recorded by a device 19, which may be a pen recorder.

The clock 20 through a lead 21 also controls the valve 9 so that it is changed over at equal intervals of time duration T.

FIG. 3 shows the variation of the measuring signal at the terminals 14 and 15 of the cell 6 when a zero reference fluid is used and at the instant $t_0$ the concentration of the measuring fluid abruptly changes from zero to the value $S_1$. The graph clearly shows that the analogous response time is six times the chosen time T. The graph further shows that the measuring signal is adjusted to a mean value in the form of a sawtooth via an exponential envelope. Nevertheless arithmetical processing of the signal, as proposed according to the invention, makes it possible to obtain a quantity which represents the measuring value $S_1$ at the output 18 of FIG. 2 after 2 cycles, that is at the instant $t_1$.

To illustrate the method of FIG. 3 shows a cycle $T_{n-1}$ and $T_n$, illustrating that, by integrating the measuring signal, noise on this signal at frequencies higher than $1/T$ is removed by filtering and direct-voltage signals are eliminated by the regular alternation of addition and subtraction indicated by the signs $-$ and $+$.

FIG. 4 shows an apparatus in which the methods according to the invention are carried out and which is largely identical with the apparatus of FIG. 2 so that the same reference characters are used for corresponding component parts.

As described in the above-mentioned U.S. patent, a reference or calibrating fluid is preferably derived from the fluid to be measured by inserting a cleaning filter in the fluid flow so that the constituents to be measured are absorbed or neutralized, for if the measuring cell is responsive to constituents other than those to be measured, in the said method when combined with the methods according to the invention the measuring cell will deliver a continuous additional signal in response to the non-specific constituents. When this signal is constant or varies linearly with time, the contribution to the ultimate measuring value will be zero owing to the choice of the successive integrating cycles of ½T for the summation and difference operations, as is indicated in FIG. 3 by the polarity signs. For this purpose In FIG. 4 the input pipe is divided into a branch 26 which includes a filter 22 for removing the constituents to be measured from the fluid, and into a branch 23. Downstream of the filter 22 the pipe 26 is connected to one inlet port of the change-over valve 9, while the pipe 23 is directly connected to the other inlet port of the valve 9. A calibrating source 11 which contains a known amount of the constituents to be measured can be connected to a branch 24 upstream of the cell 6 in order to displace the measuring range of the cell to a straight-line portion of the cell characteristic which shows the relationship between the concentration of the constituents to be measured and the output signal. For many measuring cells this characteristic is non-linear and the cell is more sensitive at high concentrations.

As an alternative, the calibrating source 11 can be connected to a tapping 25 disposed between the filter 22 and the valve 9 so that instead of a zero reference fluid a calibrating reference fluid is used.

FIG. 5 shows an apparatus which is largely identical to the apparatus of FIG. 4.

However, the measuring signal, which may or may not be processed and is taken from the output 18 of the device 16 or from the terminals 14 and 15 respectively, is not used for recording purposes in the device 19 but controls a servo system 27 an output 28 of which is connected to the calibrating source 11. The calibrating source 11 supplies a known, and in this embodiment adjustable, amount of constituents to be measured to the branch 25 in the pipe 26. For this purpose the calibrating source 11 comprises a supply container and a regulating device 29 which is set via a connection 30 by the signal from servo output 28. The calibrating source 11 supplies a known amount of the constituents to be measured which is variable in accordance with the said setting. In its simplest form the regulating device may be a rotary valve which is controlled by the servo system 27 by means of a servo motor. The calibrating source also may take the form of the universal calibrating apparatus described in our copending U.S. patent application Ser. No. 474,809. The resulting regulating circuit operates as follows: terminals 14 and 15 or terminal 18 deliver an alternating-voltage signal if the concentration in the pipe 23 and the part of the pipe 26 after the branch 25 are not equal. This signal actuates the servo system 27 so as to adjust the regulating device 29 in a direction which makes the said concentrations equal. The ultimate setting of the regulating device in response to the control provided by the servo system 27 is proportional to the amount of constituents to be determined so that, for example at an output 31, a signal is available to the recording device 19.

FIG. 6 is a graph illustrating the advantages of the signal processing method according to the invention.

Signals which are superposed on a sawtooth signal 33 to be measured, such as for example an additional calibrating signal 32, furnish zero contributions to the measuring signal 33, provided that the number of times they occur is equal in each half period. In the apparatus shown in FIG. 4 this is obtainable by driving the calibrating source 11 periodically at a frequency $2n/T$, for example $2/T$, so that a calibrating amount of constituents is pulsatorily supplied to the branch 24. FIG. 6 shows that in this case during each pair of periods T two positive contributions and two negative contributions are provided, which cancel each other.

The value of this calibrating signal can be determined by means of filtering techniques using synchronizing means having a control frequency equal to the frequency at which the calibrating fluid is supplied.

Signals 33, 34 and 36 are removed by filtering because they have a low-frequency nature relative to the calibrating frequency. With respect to the calibrating signal, the total time constant of the filter system is permitted to be many times the period T because the calibrating signal is used to correct a sensitivity drift of the measuring cell. It has been found that this drift is very slow so that an instantaneously representative calibrating signal is always obtained.

In FIG. 6 a linearly increasing interference signal is indicated by a straight line 34. A broken line 35 indicates a mean value formed by the half periods denoted by a plus sign. However, the same mean value is obtained by adding the first half of the first period to the second half of the second period. This mean value is subtracted from the firstmentioned mean value, so that here also the contribution to the measuring signal is zero.

A second sawtooth measuring signal is designated by reference number 36. The period again is T and the phase shift relative to the other measuring signal 33 is 90° or in this case a time of ½T. Because a portion 37 of minus sign is equal to a portion 38 it will be evident that one shaded right-angled triangle of minus sign is equal to the other shaded rightangled triangle of plus sign.

Hence the contribution of the measuring signal 36 to the measuring signal 33 and vice versa is zero. This shows that the two measuring systems can be arranged in parallel with the use of a single measuring cell.

FIG. 7 shows an apparatus in which a method according to the invention is used for measuring the amount of NO and $NO_2$ contained in a gas, for example air. The measuring cell 6 is sensitive to $NO_2$ only.

The circuit diagram is substantially identical to that of FIG. 4, however, gas processing is different. Under the control of the clock 20 via a lead 21a a valve 9a occupies a position a during a fraction of the time T/2, a valve 9b also occupying its position a. Air containing NO and $NO_2$ is supplied through the latter valve via a pipe 26 to the filter 22 which reduces the $NO_2$ to NO. This may be effected by means of $FESO_4$ coated on pumice grains. The resulting gas flow passes through a drying column 43 in which any water vapour present is removed. Through the branch 25 a calibrating source 11 adds a known concentration of $NO_2$ to the cleaned gas flow which then passes through the valve 9a and the measuring cell 6. As a result, a signal is obtained which may be represented by the line 32 in FIG. 6. For the rest of the time the valve 9a is in the position b and receives an air flow through a pipe 39. In the position b of the valve 9a the air drawn through the input 10 is passed through a valve 9c in its position a to the pipe 23. During a time T the gaseous $NO_2$ in the air provides a contribution to the signal at the terminals 14 and 15 of the cell 6. During the next subsequent period T the valve 9c under the control of the clock 20 occupies the position b so that the air containing NO and $NO_2$ passes through an oxidizer 40, which contains, for example, $MnO_2 + KHSO_4$ on pumice. As a result NO is converted to $NO_2$ so that the pipe 41 contains $NO_2$ only, the amount of which is measured in the cell 6 also. The contribution to the measuring signal is equal to or greater than that provided in the preceding period because now the sum of the initial concentration of $NO_2$ and of the $NO_2$ freshly formed from the NO is measured. In the next period T the valve 9b is switched to the position a, zero flow being supplied to the cell. Thus in general a tripartite sawtooth measuring signal is produced at the measuring cell which repeats every three periods. It is again found that after three periods T, by means of arithmetical operations in the device 16 of the above-mentioned nature as illustrated in FIG. 6, the desired information about the concentration of NO and that of $NO_2$ in the air supplied is obtainable. The recording device 19 may have an output channel 19a for the concentration of NO, an output channel 19b for the concentration of $NO_2$ and an output channel 19c for the calibrating signal. A broken line 42 indicates that the calibrating signal may be used to correct the measuring values.

It should be mentioned that in principle it is possible to measure more than two constituents by means of the method according to the invention, in a sequence as described with reference to the apparatus of FIG. 7. A number of, for example, m measuring fluid flows are successively supplied in a fixed cycle, each for a period T. To prevent crosstalk, T is preferably made smaller than $T_1$ and interference signals should not be too large. It can again be proved arithmetically that after (m + 1) periods T the m concentrations are determined.

What is claimed is:

1. A method of continuously and quantitatively determining one or more constituents of a measuring fluid, comprising the steps of passing a given amount of the fluid through a measuring cell which produces a measuring signal which is a measure of the amount of the constituents to be measured in the measuring fluid, the measuring cell having a response characteristic of exponential nature, alternately passing, during a time period T which is short relative to the period of the exponential response characteristic of the measuring cell, a reference fluid containing a known amount of the constituents to be measured and the measuring fluid to the measuring cell which derives a resulting sawtooth measuring signal, and processing said sawtooth measuring signal to determine the amount of the constituents in the measuring fluid.

2. A method as claimed in claim 1 wherein the reference fluid is prepared from the measuring fluid by first passing the measuring fluid through a cleaning filter in which the constituents to be measured are removed and then passing the cleaned fluid to the measuring cell.

3. A method as claimed in claim 1 wherein the reference fluid is prepared from the measuring fluid by first passing the measuring fluid through a filter which removes the constituents to be measured, and then adding a known amount of the constituents to be measured to the cleaned fluid at a point between the cleaning filter and the measuring cell.

4. A method as claimed in claim 1 wherein the processing step comprises, for each pair of successive periods of duration T, summing the integrated value of the sawtooth measuring signal during the first half of the second period T with A times the integrated value of the measuring signal during the second half of the first period T, summing the integrated value of the measuring signal during the second half of the second period T with A times the integrated value of the measuring signal during the first half of the first period T, where A is a positive weighting factor smaller than or equal to unity, and taking the difference between the said sums, which difference is a measure of the amount of the constituents to be measured in the measuring fluid.

5. A method as claimed in claim 4, characterized in that a mainly linear portion of the response characteristic of the measuring cell is used so that the weighting factor A is unity.

6. A method as claimed in claim 4, characterized in that the response characteristic of the measuring cell is expressed mainly by an exponential power having a time constant $T_1$ so that the weighting factor A is chosen to be equal to $\exp(-T/T_1)$.

7. Method as claimed in claim 4, characterized in that to measure the constituents of two fluid flows two measuring systems are arranged in parallel and one measuring cell is used, the periods of duration T being equal for both systems but the first system is shifted in time by one half period with respect to the second system.

8. A method as claimed in claim 4, characterized in that with a repetition time $T/2n$, where n is an integer, the method comprises the further steps of adding a calibrating amount of the constituents to be measured into the measuring cell, electrically filtering the sawtooth measuring signal at a frequency of $2n/T$ and measuring the mean amplitude of the resulting filtered signal and determining by means of a divider circuit a quantity which, irrespective of the sensitivity variation of the measuring cell, is proportional to the amount of the measuring fluid constituents to be measured.

9. A method as claimed in claim 3 comprising the further step of applying the measuring signal to a control loop so that the known amount of said constituents is automatically set to a value at which the sawtooth component in the measuring signal is reduced to a minimum value, the setting of the known amount of the constituents to be measured being directly proportional to the amount of the measuring fluid constituents to be determined.

10. A method as claimed in claim 1 wherein successive time periods T are of equal duration and the processing step comprises, integrating the derived sawtooth measuring signal during successive time periods T, adding first and second given parts of the integrated signal derived during one period T with first and second respective given parts of the integrated signal derived during the next successive period T to produce first and second sum signals, and subtracting said first and second sum signals to determine the amount of the constituents to be measured present in the measuring fluid.

11. Apparatus for continuously determining the quantity of one or more constituents of a measuring fluid comprising, a measuring cell having an exponential response characteristic and adapted to measure the quantity of the constituents present in the measuring fluid, means for alternately supplying the measuring fluid and a reference fluid containing a known amount of the constituents to be measured to the measuring cell in successive equal time periods T each of which is short relative to the period of the cell exponential response characteristic, the cell producing a sawtooth waveform measuring signal in response to the successive receipt of the measuring and reference fluids, timing means for controlling the operation of the means for alternately supplying the measuring fluid and reference fluid, and electronic processing and filtering means responsive to the sawtooth measuring signal of the measuring cell for providing an indication of the amount of said constituents in the measuring fluid in a time period shorter than the period of the cell exponential response characteristic.

12. Apparatus as claimed in claim 11 wherein said means for alternately supplying the measuring and reference fluids comprises a change-over valve having first and second inputs coupled to a source of measuring fluid and a source of reference fluid, respectively, and an output coupled to the input of the measuring cell, and said timing means controls the operation of the change-over valve to cause same to switch between the first and second inputs during successive equal time periods T.

13. Apparatus as claimed in claim 12 wherein the source of reference fluid comprises, a filter coupled to the source of measuring fluid for removing the constituents to be measured, and a source of calibrating fluid coupled between the filter and the measuring cell for providing a known amount of the constituents to be measured into the filtered fluid.

14. Apparatus as claimed in claim 13 further comprising a control loop coupled between the output of the measuring cell and the source of calibrating fluid, said control loop including means responsive to the measuring signal for adjusting the amount of said constituents added to the filtered fluid by the calibrating source in a sense to reduce to a minimum value the sawtooth component of the measuring signal.

15. Apparatus as claimed in claim 11 wherein the processing means comprises, means for integrating the sawtooth measuring signal, means for adding the integrated sawtooth signal occurring during the first half of the second period T to the integrated sawtooth signal occurring during the second half of the first period T to derive a first sum signal, means for adding the integrated sawtooth signal occurring during the second half of the second period T to the integrated sawtooth signal occurring during the first half of the first period T to derive a second sum signal, and means for subtracting said first and second sum signals.

16. Apparatus as claimed in claim 11 wherein said means for alternately supplying the measuring and reference fluids comprises a change-over valve having first and second inputs coupled to a source of measuring fluid and a source of reference fluid, respectively, and an output coupled to the input of the measuring cell, and means for coupling the timing means to said processing means to control its operation and to the change-over valve to cause same to switch between the first and second inputs during successive equal time periods T.

* * * * *

UNITED STATES PATENT AND TRADEMARK OFFICE
CERTIFICATE OF CORRECTION

PATENT NO. : 3,949,599
DATED : April 13, 1976
INVENTOR(S) : JOHAN C. W. KRUISHOOP It is certified that error appears in the above-identified patent and that said Letters Patent are hereby corrected as shown below:

<u>ON THE TITLE PAGE</u> cancel "METHOD OF QUANTITAVE ANALYSIS" and insert -- A METHOD OF AND APPARATUS FOR QUANTITAVE ANALYSIS --;

Abstract, line 12, after "calibrating" insert -- source of the reference fluid in an automatic zero control --;

col. 1, line 20, after "and" insert -- which --;

line 43, cancel "valve" and insert -- value --;

col. 2, line 66, cancel "adjustment" and insert -- response --;

col. 4, line 38, after "20" insert a comma (,); after "21" insert a comma (,);

line 49, after "Nevertheless" insert a comma (,);

claim 7, line 1, cancel "Method" and insert -- A method --;

Signed and Sealed this

Fourteenth Day of September 1976

[SEAL]

Attest:

RUTH C. MASON
*Attesting Officer*

C. MARSHALL DANN
*Commissioner of Patents and Trademarks*